United States Patent
Feuerbach et al.

(10) Patent No.: US 7,579,362 B2
(45) Date of Patent: Aug. 25, 2009

(54) AZA-BICYCLOALKYL ETHERS AND THEIR USE AS ALPHA7-NACHR AGONISTS

(75) Inventors: Dominik Feuerbach, Mullheim (DE); Konstanze Hurth, Saint Louis (FR); Timothy J Ritchie, London (GB)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 11/823,312

(22) Filed: Jun. 26, 2007

(65) Prior Publication Data
US 2007/0249617 A1 Oct. 25, 2007

Related U.S. Application Data

(63) Continuation of application No. 10/526,759, filed as application No. PCT/EP03/09772 on Sep. 3, 2003, now abandoned.

(30) Foreign Application Priority Data
Sep. 4, 2002 (GB) ................................ 0220581.3

(51) Int. Cl.
| | |
|---|---|
| A61K 31/4418 | (2006.01) |
| A61K 31/439 | (2006.01) |
| C07D 453/02 | (2006.01) |
| C07D 487/08 | (2006.01) |
| A61K 31/4412 | (2006.01) |
| C07D 401/14 | (2006.01) |
| A61P 25/00 | (2006.01) |
| A61K 31/4545 | (2006.01) |
| A61K 31/506 | (2006.01) |
| A61K 31/501 | (2006.01) |

(52) U.S. Cl. .................. 514/305; 546/137; 546/183; 546/276.7; 544/238; 544/315; 514/339
(58) Field of Classification Search .................. 514/305, 514/339; 546/137, 183, 276.7
See application file for complete search history.

(56) References Cited

U.S. PATENT DOCUMENTS

| | | | |
|---|---|---|---|
| 4,921,860 | A | 5/1990 | Cliffe |
| 5,385,912 | A | 1/1995 | Neuenschwander et al. |
| 5,494,918 | A | 2/1996 | Neuenschwander et al. |
| 5,612,352 | A | 3/1997 | Brown et al. |

FOREIGN PATENT DOCUMENTS

| | | |
|---|---|---|
| EP | 0149088 | 1/1989 |
| EP | 0 306 148 B1 | 3/1989 |
| EP | 0370415 | 11/1989 |
| EP | 0458214 | 5/1991 |
| GB | 2208385 | 8/1988 |
| JP | 06-293768 A | 10/1994 |
| JP | 08-502481 T | 3/1996 |
| JP | 2002-030084 A | 1/2002 |
| WO | 9215579 | 9/1992 |
| WO | 9321184 | 10/1993 |
| WO | WO 94/08992 A1 | 4/1994 |
| WO | 9531458 | 11/1995 |
| WO | 9711072 | 3/1997 |
| WO | WO 99/03859 A1 | 1/1999 |
| WO | WO 01/29034 A1 | 4/2001 |
| WO | 0160821 | 8/2001 |
| WO | WO 01/85727 A | 11/2001 |
| WO | WO 02/15662 A2 | 2/2002 |
| WO | 03051874 | 6/2003 |
| WO | 2004016608 | 2/2004 |
| WO | 03037896 | 5/2008 |

OTHER PUBLICATIONS

Lubin, et al., Annals N. Y. Acad. Sci., 628-632, 1999.*
Plummer, et al., Respiratory Research, 2005, 6:29.*
Salamone, et al., McGill J. Med., 2000, 5:90-97.*
Kalamida, et al., FEBS Journal, 274 (2007), 3799-3845.*
Martha U. Gillette et al., Role of the M1 Receptor In Regulating Circadian Rhythms, Life Sciences 68, 2001, pp. 2467-2472, Elsevier Science Inc., USA.
Sandrine N. Hardouin et al.; Altered Cardiovascular Reponses in Mice Lacking the M1 Muscarinic Acetylcholine Receptor, The Journal of Pharmacology and Experimental Therapeutics, 2002, pp. 129-137, vol. 301, No. 1, The American Society for Pharmacology and Experimental Therapeutics, USA.
Malcolm J. Sheardown, Muscarinic M1 Receptot Agonists and M2 Receptor Antagonists as Therapeutic Targets in Alzheimer's Disease, Expert Opin. Ther. Patents, 2002, pp. 863-870, Ashley Publications.
Harumi Kitagawa et al., Safety, Pharmacokinetics, and Effect on Cognitive Function of Multiple Doses of GTS-21 in Healthy, Male Volunteers, Neuropsychopharmacology, 2003, pp. 542-551, 28, Nature Publishing Group.

* cited by examiner

Primary Examiner—Mark L Berch
Assistant Examiner—Cecilia M Jaisle
(74) Attorney, Agent, or Firm—Foley & Lardner LLP

(57) ABSTRACT

The present invention relates to 1-aza-bicycloalkyl derivatives of formula I,

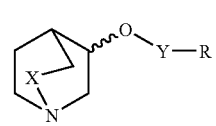

(I)

wherein X is CH$_2$ or a single bond; Y is a group of formula

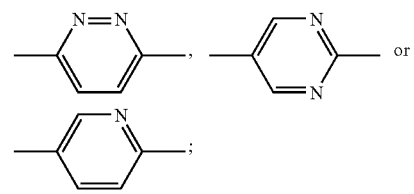

and wherein R has the meanings as defined in the specification, which compounds are alpha 7 nicotinic acetylcholine receptor (nAChR) agonists;
to processes for their production, their use as pharmaceuticals and to pharmaceutical compositions comprising them.

13 Claims, No Drawings

AZA-BICYCLOALKYL ETHERS AND THEIR USE AS ALPHA7-NACHR AGONISTS

This is a continuation of application Ser. No. 10/526,759 filed on Aug. 3, 2005, which is National Stage of International Application No. PCT/EP03/09772 filed on Sep. 3, 2003, the entire disclosures of which are hereby incorporated by reference.

The present invention relates to novel 1-aza-bicycloalkyl derivatives, to processes for their production, their use as pharmaceuticals and to pharmaceutical compositions comprising them.

More particularly the present invention provides in a first aspect, a compound of formula I

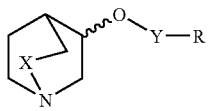

(I)

wherein
X is $CH_2$ or a single bond;
Y is a group of formula

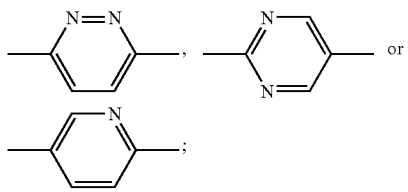

or

R is a substituted or unsubstituted $C_5$-$C_{10}$ aryl or substituted or unsubstituted hetero-$C_8$-$C_{10}$aryl, $N(R^1)(R^4)$, or $N(R^2)(CHR^3R^4)$;
each of $R^1$, $R^2$ and $R^3$ is independently H, $C_{1-4}$alkyl, or $CF_3$;
$R^4$ is a substituted or unsubstituted $C_5$-$C_{10}$ aryl or substituted or unsubstituted hetero-$C_8$-$C_{10}$ aryl;
in free base or acid addition salt form.

$C_5$-$C_{10}$ aryl and hetero-$C_5$-$C_{10}$ aryl as used herein mean especially partially or fully unsaturated, e.g. aromatic, residues optionally substituted by one or more substituents, preferably up to three substituents, selected from halogen, e.g. F, Cl, Br, I; CN; $C_1$-$C_4$alkyl, such as methyl, ethyl or propyl, $CrC_4$alkenyl, such as vinyl, $C_2$-$C_4$alkinyl, which radicals themselves can be unsubstituted or substituted by halogen, e.g. difluoromethyl or trifluoromethyl; $C_1$-$C_4$alkoxy, which radical itself can be unsubstituted or substituted by halogen, e.g. trifluoromethoxy; formyl, acetyl; $C_1$-$C_3$alkoxycarbonyl; N,N-dl-($C_1$-$C_3$alkyl) carbamoyl; phenyl, phenoxy; or which substituents can be condensed, e.g. to a benzo[1,3]dioxole or 2,3-dihydrobenzo[1,4]dioxine and/or to a further heterocyclic ring. Hetero-$C_5$-$C_{10}$ aryl is an aromatic heterocyclic system comprising one, two or three hetero atoms selected from N, O, S, e.g. a 5 or 7 membered aromatic heterocyclic residue optionally condensed, e.g. to 1 or 2 phenyl rings and/or to a further heterocyclic ring. Examples of $C_5$-$C_{10}$ aryl or hetero-$C_5$-$C_{10}$aryl residues as mentioned above include phenyl, naphthyl, tetrahydronaphthyl such as tetralinyl, indanyt, thienyl, benzothienyl, furanyl, benzofuranyl and isobenzofuranyl.

Preferably, $C_5$-$C_{10}$aryl and hetero-$C_5$-$C_{10}$aryl as used herein mean partially or fully unsaturated, e.g. aromatic, residues optionally substituted by one or more substituents, preferably up to three substituents, selected from halogen, e.g. F, Cl, Br, I; CN; $C_1$-$C_4$alkyl, such as methyl, ethyl or propyl, which radical Itself can be unsubstituted or substituted by halogen, e.g. difluoromethyl or trifluoromethyl; $C_1$-$C_4$alkoxy, which radical itself can be unsubstituted or substituted by halogen, e.g. trifluoromethoxy; or which substituents can be condensed, e.g. to a benzo[1,3]dioxole or 2,3-dihydrobenzo[1,4]dioxine and/or to a further heterocyclic ring. Hetero-$C_5$-$C_{10}$aryl is an aromatic heterocyclic system comprising one, two or three hetero atoms selected from N, O, S, e.g. a 5 or 7 membered aromatic heterocyclic residue optionally condensed, e.g. to 1 or 2 phenyl rings and/or to a further heterocyclic ring. Examples of $C_5$-$C_{10}$aryl or hetero-$C_5$-$C_{10}$aryl residues as mentioned above include phenyl, naphthyl, indanyl, tetralinyl, thienyl, benzothienyl, furanyl, benzofuranyl and Isobenzofuranyl.

Acid addition salts are especially pharmaceutically acceptable salts of compounds of formula I. For Isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred.

On account of the asymmetrical carbon atom(s) present in the compounds of formula I and their salts, the compounds may exist in optically active form or in form of mixtures of optical isomers, e.g. in form of racemic mixtures. All optical Isomers and their mixtures including the racemic mixtures are part of the present invention.

In formula I the following significances are preferred independently, collectively or in any combination or sub-combination, if applicable:

(a) X is $CH_2$;

(b) Y is 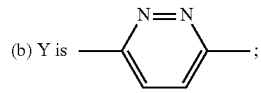;

(c) Y is 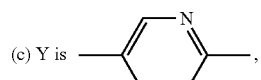, (d) R is 1-isobenzofuranyl or substituted or unsubstituted phenyl, e.g. monosubstituted by a chlorine or fluorine in position 2, 3 or 4, $CF_3$ in position 2 or 3, methoxy in position 2; trifluoromethoxy in position 3; benzo[1,3]-dioxole; 2,3-dihydrobenzo[1,4]-dioxine; cyano; or disubstituted, e.g. by a fluorine in position 2 and 5, 3 and 5 or chlorine in position 2 and fluorine in position 6.

Preferred are those aza-bicycloalkyl derivatives of formula I wherein
X is $CH_2$ or a single bond;
Y is a group of formula

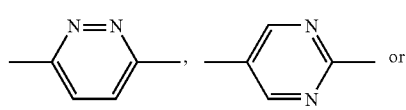 or

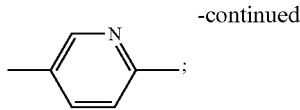

and

R is phenyl, naphthyl, tetrahydronaphthyl, indanyl, thienyl, benzothienyl, furanyl, benzofuranyl and isobenzofuranyl, which in each case can be unsubstituted or mono-, di- or trisubstituted by halogen, cyano, formyl, acetyl, $C_1$-$C_3$alkoxycarbonyl, N,N-di-($C_1$-$C_3$alkyl) carbamoyl, phenyl, phenoxy, methylendioxy, ethylendioxy; or $C_1$-$C_4$alkyl, $C_2$-$C_4$alkenyl, $C_2$-$C_4$alkenyl or $C_1$-$C_4$alkoxy, which radicals themselves can be unsubstituted or mono-, di- or trisubstituted by halogen.

More preferred are those aza-bicycloalkyl derivatives of formula I wherein

X is $CH_2$ or a single bond;

Y is a group of formula

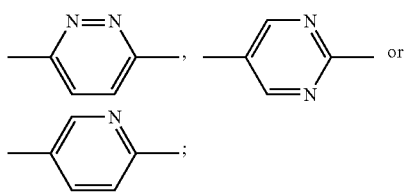

and

R is (a) phenyl which is unsubstituted or mono-, di- or trisubstituted by halogen, cyano, methylendioxy, $C_1$-$C_4$alkyl, which is unsubstituted or mono-, di- or trisubstituted by halogen, or $C_1$-$C_4$alkoxy, which is unsubstituted or mono-, di- or trisubstituted by halogen, (b) naphthyl, indanyl, tetralinyl or (c) furanyl, benzofuranyl, isobenzofuranyl, benzothienyl or thienyl, in free base or acid addition salt form.

Even more preferred are those aza-bicycloalkyl derivatives of formula I wherein

X is $CH_2$ or a single bond;

Y is a group of formula

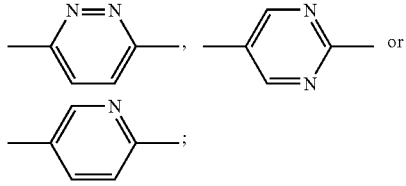

and

R is (a) phenyl which is unsubstituted or mono-, di- or trisubstituted by halogen, cyano, methylendioxy, $C_1$-$C_4$alkyl, which is unsubstituted or mono-, di- or trisubstituted by halogen, or $C_1$-$C_4$alkoxy, which is unsubstituted or mono-, di- or trisubstituted by halogen, (b) naphthyl, or (c) furanyl, benzofuranyl, isobenzofuranyl, or thienyl, in free base or add addition salt form.

In addition to the foregoing the present invention also provides a process for the production of a compound of formula I, which process comprises the step of reacting a compound of formula II $$z\text{—}Y\text{—}R \qquad (II);$$

wherein Y and R are as defined above and z is a leaving group, e.g. F, Cl, Br, I or $OSO_2CF_3$, with a compound of formula III

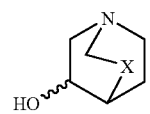

(III)

wherein X is as defined above for a compound of formula I, and recovering the so obtained compound of formula I in free base or acid addition salt form.

The reaction may be carried out in accordance with standard procedures, for instance, as illustrated in the Examples.

Compounds of formula II are known or may be prepared from corresponding known compounds, e.g. as described in the Examples, e.g. in analogy to Coates W J, McKillop A (1992) Synthesis 334-342. The compounds of formula III are known.

Alternatively, the compounds of formula I'

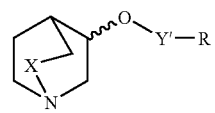

(I')

wherein

X and R are as defined above and Y' is

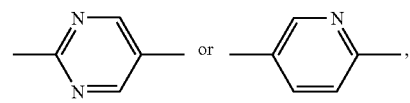

can be produced by a process comprising the step of reacting a compound of formula IV

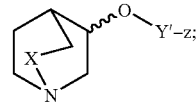

(IV)

wherein Y', z and X are as defined above, with a compound of formula V

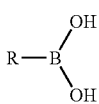 (V)

wherein R is as defined above for a compound of formula I, and recovering the so obtained compound of formula I' in free base or acid addition salt form.

Compounds of formula IV are known or may be prepared from corresponding known compounds, e.g. as described in Example 17, e.g. by reacting compounds of formula III with compounds of formula II';

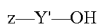 (II);

wherein Y' is

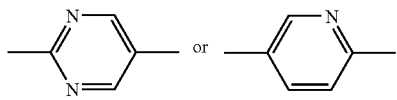

or and z is as described above.

Compounds of formula V (e.g. unsubstituted or substituted phenylboronic acids) are known or may be prepared from corresponding known compounds. For instance, a compound of formula VI,

 (VI)

wherein R has the meaning as provided for a compound of formula I, can be reacted with a trialkyl borate in an inert solvent such as benzene, toluene, tetrahydrofuran or mixtures thereof by the addition of butyl lithium at a temperature of between about −78° C. and −25° C., e.g. about −40° C., for a period of about 1 hour to 6 hours, furnishing a compound of formula V.

Working up the reaction mixtures according to the above processes and purification of the compounds thus obtained may be carried out in accordance to known procedures.

Acid addition salts may be produced from the free bases in known manner, and vice-versa. Suitable acid addition salts for use in accordance with the present invention include, for example, the hydrochloride and the formate.

Compounds of formula I in optically pure form can be obtained from the corresponding racemates according to well-known procedures, e.g. HPLC with chiral matrix. Alternatively, optically pure starting materials can be used.

Stereoisomeric mixtures, e.g. mixtures of diastereomers, can be separated into their corresponding isomers in a manner known per se by means of suitable separation methods. Diastereomeric mixtures for example may be separated into their individual diastereomers by means of fractionated crystallization, chromatography, solvent distribution, and similar procedures. This separation may take place either at the level of a starting compound or in a compound of formula I itself. Enantiomers may be separated through the formation of diastereomeric salts, for example by salt formation with an enantiomer-pure chiral acid, or by means of chromatography, for example by HPLC, using chromatographic substrates with chiral ligands.

In the additional process steps, carried out as desired, functional groups of the starting compounds which should not take part in the reaction may be present in unprotected form or may be protected for example by one or more of the protecting groups mentioned below. The protecting groups are then wholly or partly removed according to one of the methods described there.

The protecting groups may already be present in precursors and should protect the functional groups concerned against unwanted secondary reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. The specialist knows, or can easily establish, which protecting, groups are suitable with the reactions mentioned hereinabove and hereinafter.

The protection of such functional groups by protecting groups, the protecting groups themselves, and their removal reactions are described for example in standard reference works, such as J. F. W. McOmie, "Protective Groups in Organic Chemistry", Plenum Press, London and New York 1973, in T. W. Greene, "Protective Groups in Organic Synthesis", Wiley, New York 1981, in "The Peptides"; Volume 3 (editors: E. Gross and J. Melenhoter), Academic Press, London and New York 1981, in "Methoden der organischen Chemie" (*Methods of organic chemistry*) Houben Weyl, 4th edition, Volume 15/I, Georg Thieme Verlag, Stuttgart 1974, in H.-D. Jakubke and H. Jescheit, "Aminosäuren, Peptide, Proteine" (Amino acids, peptides, proteins), Verlag Chemle, Weinheim, Deerfield Beach, and Basel 1982, and in Jochen Lehmann, "Chemie der Kohlenhydrate: Monosaccharide und Derivate" (*Chemistry of carbohydrates: monosaccharides and derivatives*), Georg Thieme Verlag, Stuttgart 1974.

All process steps described here can be carried out under known reaction conditions, preferably under those specifically mentioned, in the absence of or usually in the presence of solvents or diluents, preferably such as are inert to the reagents used and able to dissolve these, in the absence or presence of catalysts, condensing agents or neutralising agents, for example Ion exchangers, typically cation exchangers, for example in the H+ form, depending on the type of reaction and/or reactants at reduced, normal, or elevated temperature, for example in the range from −100° C. to about 190° C., preferably from about −80° C. to about 150° C., for example at −80 to −60° C., at room temperature, at −20 to 40° C. or at the boiling point of the solvent used, under atmospheric pressure or in a closed vessel, where appropriate under pressure, and/or in an inert atmosphere, for example under argon or nitrogen.

The compounds of the invention and their pharmaceutically acceptable acid addition salts, hereinafter referred to as agents of the invention, exhibit valuable pharmacological properties when tested in vitro and in animals, and are therefore useful as pharmaceuticals.

In particular, the agents of the invention are α7 nicotinic acetylcholine receptor (nAChR), agonists.

In functional assays, the agents of the invention display high affinity at the α7 nAChR as shown in the following tests:

a) A functional assay for affinity at the α7 nAChR is carried out with a rat pituitary cell line stably expressing the α7 nAChR. As a read out, the calcium influx upon stimulation of the receptor is used. In this assay, agents of the invention exhibit pEC$_{50}$ values of about 5 to about 8.

b) To assess the activity of the agents of the invention on the human neuronal nAChR α 4β2, a similar functional assay is carried out using a human epithelial cell line stable expressing the human α4β2 subtype. In this assay, agents of the invention show selectivity for the α7 nAChR subtypes.

c) To assess the activity of the compounds of the invention on the "ganglionic subtype" and the muscle type of nicotinic receptor, similar functional assays as described under a) are carried out with a human epithelial cell line stably expressing the human ganglionic subtype or a cell line endogenously expressing the human muscle type of nicotinic receptors. In these assays, agents of the invention display no or little activity on the ganglionic and muscle type of nicotinic receptor subtypes.

In the model of mice showing sensory gating deficit (DBA/2-mice) described by S. Leonard et al. in Schizophrenia Bulletin 22, 431-445 (1996), the agents of the invention induce significant sensory gating at concentrations of about 10 to about 40 μM.

The agents of the invention are therefore useful for the prevention and treatment of psychotic disorders such as schizophrenia, mania, depression and anxiety, and for the prevention and treatment of neurodegenerative disorders such as senile dementia, Alzheimer's disease and other intellectual impairment disorders, such as attention deficit hyperactivity disorders (ADHD); Parkinson's disease, Huntington's chorea, amyotrophic lateral sclerosis, multiple sclerosis, epilepsy, convulsions, Tourette syndrome, OCD (obsessive compulsive disorder), neuropathic, postoperative and inflammatory pain, phantom limb pain, cognition, smoking cessation, memory deficits and dysfunction, learning deficit, panic disorders, narcolepsy, nociception, AIDS dementia, senile dementia, autism, tardive dyskinesia, social phobia, pseudodementia. The usefulness of α7 nAChR agonists in neurodegeneration is documented in the literature, e.g. in Wang et al., J. biol. Chem. 275, 5626-5632 (2000).

For the above indications the appropriate dosage of the agents of the invention will, of course, vary depending upon, for example, the host, the mode of administration and the nature and severity of the condition being treated as well as the relative potency of the particular agent of the invention employed. For example, the amount of active agent required may be determined on the basis of known in vitro and in vivo techniques, determining how long a particular active agent concentration in the blood plasma remains at an acceptable level for a therapeutic effect. In general, satisfactory results in animals are indicated to be obtained at daily dosages of from about 0.01 to about 20.0 mg/kg p.o. in humans, an indicated daily dosage is in the range of from about 0.7 to about 1400 mg/day p.o., e.g. from about 50 to 200 mg (70 kg man), conveniently administered once or in divided doses up to 4× per day or in sustained release form. Oral dosage forms accordingly suitably comprise from about 1.75 or 2.0 to about 700 or 1400 mg of an agent of the invention admixed with an appropriate pharmaceutically acceptable diluent or carrier therefor.

Examples for compositions comprising an agent of the invention include, e.g. a solid dispersion, an aqueous solution, e.g. containing a solubilising agent, a microemulsion and a suspension of, e.g. a hydrochloride salt of a compound of formula I in the range of from 0.1 to 1%, e.g. 0.5%. The composition may be buffered to a pH in the range of, e.g. from 3.5 to 9.5, e.g. to pH 4.5, by a suitable buffer.

The agents of the invention are also useful as research chemicals.

For use according to the invention, the agent of the invention may be administered as single active agent or in combination with other active agents commonly employed for the treatment of the disorders mentioned herein, in any usual manner, e.g. orally, for example in the form of tablets or capsules, or parenterally, for example in the form of injection solutions or suspensions.

The pharmaceutical compositions for separate administration of the combination partners and for the administration in a fixed combination, i.e. a single galenical composition comprising at least two combination partners, according to the invention can be prepared in a manner known per se and are those suitable for enteral, such as oral or rectal, and parenteral administration to mammals, including man, comprising a therapeutically effective amount of at least one pharmacologically active combination partner alone or in combination with one or more pharmaceutically acceptable carries, especially suitable for enteral or parenteral application.

Pharmaceutical compositions contain, for example, from about 0.1% to about 99.9%, preferably from about 20% to about 60%, of the active ingredients. Pharmaceutical preparations for the combination therapy for enteral or parenteral administration are, for example, those in unit dosage forms, such as sugar-coated tablets, tablets, capsules or suppositories, and furthermore ampoules. If not indicated otherwise, these are prepared in a manner known per se, for example by means of conventional mixing, granulating, sugar-coating, dissolving or lyophilizing processes. It will be appreciated that the unit content of a combination partner contained in an individual dose of each dosage form need not in itself constitute an effective amount since the necessary effective amount can be reached by administration of a plurality of dosage units.

In particular, a therapeutically effective amount of each of the combination partners may be administered simultaneously or sequentially and in any order, and the components may be administered separately or as a fixed combination. For example, the method of delay of progression or treatment of a proliferative disease according to the invention may comprise (i) administration of the combination partner (a) in free or pharmaceutically acceptable salt form and (ii) administration of a combination partner (b) in free or pharmaceutically acceptable salt form, simultaneously or sequentially in any order, in jointly therapeutically effective amounts, preferably in synergistically effective amounts, e.g. in daily dosages corresponding to the amounts described herein. The individual combination partners can be administered separately at different times during the course of therapy or concurrently in divided or single combination forms. Furthermore, the term administering also encompasses the use of a pro-drug of a combination partner that convert in in vivo to the combination partner as such. The instant invention is therefore to be understood as embracing all such regimes of simultaneous or alternating treatment and the term "administering" is to be interpreted accordingly.

The effective dosage of each of the combination partners employed may vary depending on the particular compound or pharmaceutical composition employed, the mode of administration, the condition being treated, the severity of the condition being treated. Thus, the dosage regimen is selected in accordance with a variety of factors including the route of administration and the renal and hepatic function of the patient. A physician, clinician or veterinarian of ordinary skill can readily determine and prescribe the effective amount of the single active ingredients required to prevent, counter or arrest the progress of the condition. Optimal precision in achieving concentration of the active ingredients within the range that yields efficacy without toxicity requires a regimen based on the kinetics of the active ingredients' availability to target sites.

In accordance with the foregoing, the present invention also provides:
(1) An agent of the invention for use as an alpha-7 receptor agonist, for example for use in any of the particular indications hereinbefore set forth.
(2) A pharmaceutical composition comprising an agent of the invention as active ingredient together with a pharmaceutically acceptable diluent or carrier therefore.
(2') A pharmaceutical composition for the treatment or prevention of a disease or condition in which alpha-7 receptor activation plays a role or is implicated comprising an agent of the invention and a carrier.
(3) A method for the treatment of any of particular indication hereinbefore set forth in a subject in need thereof which comprises administering an effective amount of an agent of the invention.
(3') A method for treating or preventing a disease or condition in which the alpha-7 receptor activation plays a role or is implicated comprising administering to a mammal in need thereof a therapeutically effective amount of an agent of the invention.
(4) The use of an agent of the invention for the manufacture of a medicament for the treatment or prevention of a disease or condition in which the alpha-7 receptor activation plays a role or is implicated.
(5) A method as defined above comprising co-administration, e.g. concomitantly or in sequence, of a therapeutically effective amount of an alpha-7 agonist, e.g. an agent of the invention and a second drug substance, said second drug substance being for example for use in any of the particular indications hereinbefore set forth.
(6) A combination comprising a therapeutically effective amount of an alpha-7 agonist agonist, e.g. an agent of the invention and a second drug substance, said second drug substance being for example for use in any of the particular indications hereinbefore set forth.

The following Examples illustrate the invention.

Abbreviations Used in the Examples

AcOEt ethyl acetate
aq. aqueous
DEAD diethylazodlcarboxylate
DMF dimethylformamide
EtOH ethanol
FC flash chromatography
h hour
HV high vacuum
MeOH MeOH
RP-HPLC reversed-phase high performance liquid chromatography
rt room temperature
rac. racemate
soln. solution
TFA trifluoroacetic acid
THF tetrahydrofuran

EXAMPLE 1

Preparation of (rac.)-3-[6-(4-fluorophenyl)-pyridazin-3-yloxy]-1-aza-blcyclo[2.2.2]octane A solution of (rac.)-3-qulnuclidinol (0.007 mole) in dry THF under nitrogen is treated with sodium hydride (60% in mineral oil; 1.1 equiv.). After 1 hr at room temperature, a solution of 3-chloro-6-(4-fluoro-phenyl)pyridazine (1.0 equiv.) in THF (30 ml) is added, and the reaction mixture heated to reflux for 6 hrs. After cooling to rt, the THF is evaporated and the residue dissolved in ethyl acetate (100 ml) and then washed with water (3×20 ml), followed by sodium chloride solution (20 ml). The ethyl acetate is dried over anhydrous magnesium sulfate, filtered and evaporated to dryness, and the residual oil purified by silica gel column chromatography (eluent: ethyl acetate-methanol-triethylamine (50:10:2) to afford (rac.)-3-[6-(4-fluorophenyl)-pyridazin-3-yloxy]-1-aza-bicyclo[2.2.2]octane as a colourless solid. $^1$H-NMR (400 MHz, CDCl$_3$): δ=8.00 (m, 2H), 7.75 (d, 1H), 7.17 (m, 2H), 7.1 (d, 1H), 5.35 (m, 1H), 3.5 (m, 1H), 2.99-2.83 (m, 5H), 2.32 (m, 1H), 1.98 (m, 1H), 1.76-1.68 (m, 2H), 1.46 (m, 1H).

The following compounds of formula I wherein Y is

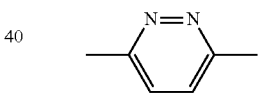

can be prepared in analogy to Example 1:

| Ex. | stereo-chem. | X | R | HPLC rt (min) | $[α]_D^{rt}$ | mp. °C. (salt) | M + H$^+$ |
|---|---|---|---|---|---|---|---|
| 2 | (3R,4S) | bond | phenyl | 5.7 | −23.5° (0.1% MeOH) | 143-145 (no salt) | 268 |
| 3 | (3S,4R) | bond | phenyl | 5.7 | −26.5° (0.1% MeOH) | 145-147 (no salt) | 268 |
| 4 | (S) | CH$_2$ | phenyl | 5.2 | −32.5° (0.5% MeOH) | 128-130 (no salt) | 282.2 |
| 5 | (R) | CH$_2$ | 4-chloro-phenyl | 6.2 | +29.0° (0.1% MeOH) | 175-177 (no salt) | 316.2 |
| 6 | (R) | CH$_2$ | 3-chloro-phenyl | 6.2 | +38.5° (0.1% MeOH) | 98-100 (no salt) | 316.2 |
| 7 | rac. | CH$_2$ | 2-methoxy-phenyl | 5.5 | N/A | 125-128 (no salt) | 312.4 |
| 8 | (R) | CH$_2$ | 4-trifluoromethyl-phenyl | 7.0 | +28 (0.1% MeOH) | 172-175 (no salt) | 350.5 |
| 9 | (R) | CH$_2$ | 2-fluoro-phenyl | 5.6 | +23.5° (0.1% MeOH) | 110-113 (no salt) | 300.2 |
| 10 | (R) | CH$_2$ | 2-chloro-phenyl | 5.7 | +29.5° (0.1% MeOH) | 85-87 (no salt) | 316.2 |

-continued

| Ex. | stereo-chem. | X | R | HPLC rt (min) | $[\alpha]_D^{rt}$ | mp. °C. (salt) | M + H⁺ |
|---|---|---|---|---|---|---|---|
| 11 | (R) | CH₂ | 4-fluoro-phenyl | 5.7 | +39.5° (0.1% MeOH) | 146-149 (no salt) | 300.2 |
| 12 | (R) | CH₂ | 3-fluoro-phenyl | 5.5 | +31.5° (0.1% MeOH) | 118-121 (no salt) | 300.2 |
| 13 | (R) | CH₂ | 3,4-dichloro-phenyl | 7.3 | +29.5° (0.1% MeOH) | 173-175 (no salt) | 350.2 |
| 14 | (R) | CH₂ | 3-trifluoromethyl-phenyl | 6.9 | +23.0° (0.1% MeOH) | 112-115 (no salt) | 350.3 |
| 15 | (R) | CH₂ | 3,5-dichloro-phenyl | 7.3 | +31.0° (0.1% MeOH) | 127-130 (no salt) | 350.2 |
| 16 | (R) | CH₂ | 1-isobenzofuranyl | 6.8 | +29.0 (0.1% MeOH) | 193-195° (no salt) | 321.38 |

EXAMPLE 17

Preparation of (rac.)-3-(5-Phenyl-pyrimidin-2-yloxy)-1-aza-blcyclo[2.2.2]octane

5-Bromo-2-hydroxy-pyrimidine (400 mg, 2.29 mmol), (rac.)-3-qulnuclidinol (432 mg, 3.36 mmol) and triphenylphosphine (890 mg, 3.40 mmol) are dissolved in THF (25 ml). After stirring for 10' at −10° C., a solution of DEAD (522 µl, 3.36 mmol) in THF (20 ml) is added dropwise. The reaction mixture is allowed to warm to rt and is stirred for 16 h at rt. The reaction mixture is evaporated to give an orange semisolid (2.50 g), which is triturated with AcOEt and filtered to give (rac.)-3-(5-bromo-pyrimidin-2-yloxy)-1-aza-bicyclo[2.2.2]-octane as a white solid. The filtrate is purified by FC (silica gel, eluents: AcOEt/MeOH 9:1, then AcOEt/MeOH/NEt₃ 70:27:3). (rac.)-3-(5-Bromo-pyrimidin-2-yloxy)-1-aza-bicyclo[2.2.2]octane (150 mg, 0.53 mmol), phenylboronic acid (66 mg, 0.54 mmol) and tetrakis(triphenylphosphine)palladium are dissolved in toluene:EtOH 9:1 (15 ml). Na₂CO₃ (225 mg, 2.12 mmol) is dissolved in water (1.5 ml) and added to the reaction mixture, which is heated at 90° C. for 20 h. After cooling to rt, it is filtered over celite; the toluene layer is separated and washed with brine. The aq. layers are re-extracted with AcOEt, the combined organic extracts are dried over MgSO₄, filtered and the filtrate is evaporated to give a light yellow gum (195 mg) that is purified by FC (silica gel, eluents: AcOEt/MeOH 9:1, then AcOEt/MeOH/NEt₃ 70:27:3) to give a white solid which still contains starting material. A second purification is done by RP-HPLC (Phenomenex RP18 column, gradient 0.08% aq. HCOOH/CH₃CN 95:5→CH₃CN in 20') to give (rac)-(5-phenyl-pyrimidin-2-yloxy)-1-aza-bicyclo[2.2.2]octane as its formate salt; HPLC rt (min): 5.4; mp ° C.: 108-114; M+H⁺ 282.2.

EXAMPLE 18

Preparation of (R)-3-(5-Phenyl-pyrimidin-2-yloxy)-1-aza-blcyclo[2.2.2]octane

5-Bromo-2-chloro-pyrimidine (400 mg, 2.03 mmol), phenylboronic acid (253 mg, 2.07 mmol) and tetrakis(triphenylphosphine)palladium (118 mg, 0.102 mmol) are dissolved in toluene/EtOH 9:1 (50 ml). Na₂CO₃ (861 mg, 8.12 mmol) is dissolved in water (4 ml) and added to the reaction mixture. The mixture is stirred at 90° C. for 19 h, cooled to rt and filtered over celite. The toluene layer is separated and washed with brine. The aq. layers are re-extracted with AcOEt; the combined organic extracts are dried over MgSO₄ and filtered. The filtrate is evaporated to give a yellow solid (503 mg), which is purified by FC (silica gel, eluents cyclohexane and AcOEt/cyclohexane 1:9) to give 2-chloro-5-phenyl-pyrimidine. (R)-3-qulnuclidinol (478 mg, 3.76 mmol) is added to a suspension of NaH (164 mg of a 60% dispersion in mineral oil, 4.09 mmol) in DMF (10 ml). The mixture is stirred for 1 h at rt. 2-Chloro-5-phenyl-pyrimidine (177 mg, 0.93 mmol) is added and the mixture is heated for 3.5 h at 90° C. The reaction mixture is diluted with toluene and washed with 1 M aq. NaOH solution and brine. The aq. layers are re-extracted with toluene (3×). The combined organic extracts dried over MgSO₄ and filtered. The filtrate is evaporated to give a yellow solid (310 mg), which is purified by FC (silica gel, eluents: AcOEt, then AcOEt/MeOH/NEt₃ 80:18:2). A second purification is done by RP-HPLC (Phenomenex RP18 column, gradient 0.08% aq. HCOOH→0.08% aq. HCOOH/CH3CN 80:20 in 10', +CH₃CN in 15') to give (R)-3-(5-phenyl-pyrimidin-2-yloxy)-1-aza-blcyclo[2.2.2]-octane as Its formate salt, HPLC rt (min): 5.4; mp ° C.: 108-110; $[\alpha]_D^{rt}$ +8.6 (1.03, MeOH), M+H⁺282.2.

The following compounds of formula I wherein —O—Y— is can be prepared in analogy to Example 17 or 18:

| Ex. | stereo-chem. | X | R | HPLC rt (min) | $[\alpha]_D^{rt}$ | mp. °C. (salt) | M + H$^+$ |
|---|---|---|---|---|---|---|---|
| 19 | (S) | CH$_2$ | phenyl | 5.6 | −31.0° (0.95% MeOH) | 126-129 (no salt) | 282.2 |
| 20 | rac. | CH$_2$ | 2-fluoro-phenyl | 5.9 | N/A | 87-93 (no salt) | 300.2 |
| 21 | rac. | CH$_2$ | 3-chloro-phenyl | 6.6 | N/A | 163-165 (no salt) | 316.2 |
| 22 | rac. | CH$_2$ | 3,4-dichloro-phenyl | 3.6 | N/A | 182-184 (no salt) | 350.1 |
| 23 | rac. | CH$_2$ | 2,4-dichloro-phenyl | 3.6 | N/A | N/A (oil) (HCl salt) | 350.1 |
| 24 | rac. | CH$_2$ | 3,5-dichloro-phenyl | 3.7 | N/A | 183-184 (no salt) | 350.1 |
| 25 | rac. | CH$_2$ | 3-cyano-phenyl | 3.5 | N/A | 189 (no salt) | 307.2 |
| 26 | rac. | CH$_2$ | 3-trifluoromethyl-phenyl | 3.5 | N/A | 158-159 (no salt) | 350.2 |
| 27 | rac. | CH$_2$ | benzo[1,3]dioxol-5-yl | 5.9 | N/A | nd (no salt) | 326.2 |
| 28 | (R) | CH$_2$ | 2-fluoro-phenyl | 5.7 | nd | nd (no salt | 300.2 |
| 29 | rac. | CH$_2$ | 3,5-bis-trifluoro-methyl-phenyl | 7.6 | N/A | nd (no salt) | 418.2 |
| 30 | (R) | CH$_2$ | 2-chloro-phenyl | 3.4 | +29.6° (0.50% EtOH) | nd (no salt) | 316.2 |
| 31 | (R) | CH$_2$ | 3-chloro-phenyl | 3.4 | nd | 160-163 (no salt) | 316.2 |
| 32 | (R) | CH$_2$ | thiophen-2-yl | 5.2 | nd | nd (no salt) | 288.1 |
| 33 | (R) | CH$_2$ | naphthalen-1-yl | 6.8 | nd | nd (no salt) | 332.2 |
| 34 | rac. | CH$_2$ | 4-chloro-phenyl | 3.5 | N/A | 170-173 (no salt) | 316.2 |
| 35 | (R) | CH$_2$ | benzofuran-2-yl | 6.9 | +33.8° (0.97% MeOH) | 183-186 (no salt) | 322.2 |
| 36 | (R) | CH$_2$ | thiophen-3-yl | 5.3 | +26.2° (0.99% MeOH) | 167-174 (no salt) | 288.1 |
| 37 | (R) | CH$_2$ | naphthalen-2-yl | 7.0 | +27.0° (0.1% MeOH) | 170-190 (no salt) | 332.2 |
| 38 | (R) | CH$_2$ | 2,3-dichloro-phenyl | 6.9 | nd | nd (no salt) | 350.1 |
| 39 | (R) | CH$_2$ | 2,3-difluoro-phenyl | 3.3 | +33.7° (0.5% MeOH) | 135-136 (no salt) | 318.2 |
| 40 | rac | CH$_2$ | 2-methoxy-phenyl | 3.4 | N/A | 160-163 (no salt) | 312.2 |
| 41 | (R) | CH$_2$ | 2,6-dichloro-phenyl | nd | nd | nd (no salt) | 350 |
| 42 | (R) | CH$_2$ | 3-fluoro-phenyl | nd | nd | nd (no salt) | 300 |
| 43 | (R) | CH$_2$ | furan-3-yl | nd | nd | nd (no salt) | 272 |
| 44 | (R) | CH$_2$ | furan-2-yl | 3.2 | nd | nd (no salt) | 272.2 |
| 45 | (R) | CH$_2$ | 2,5-difluoro-phenyl | 4.1 | +24.7° (0.525% MeOH) | nd (no salt) | 318.3 |
| 46 | (R) | CH$_2$ | 2,5-dichloro-phenyl | 5.3 | +19.9° (0.525% MeOH) | nd (no salt) | 350.2 |
| 47 | (R) | CH$_2$ | 2-trifluoromethyl-phenyl | 3.5 | nd | 187-207 (no salt) | 350.2 |
| 48 | (R) | CH$_2$ | o-tolyl | 4.4 | nd | 85-94 (no salt) | 296.2 |
| 49 | (R) | CH$_2$ | m-tolyl | 3.4 | +33.1° (0.52% MeOH) | 139-140 (no salt) | 296.2 |
| 50 | (R) | CH$_2$ | p-tolyl | 4.7 | +28.6° (0.54% MeOH) | 158-164 (no salt) | 296.2 |
| 51 | (R) | CH$_2$ | 5-fluoro-2-methoxy-phenyl | 4.5 | +25.5° (0.55% MeOH) | 115-118 (no salt) | 330.2 |
| 52 | (R) | CH$_2$ | 2-fluoro-4-methyl-phenyl | 4.9 | +30.2° (0.54% MeOH) | 130-132 (no salt) | 314.2 |
| 53 | (R) | CH$_2$ | 2-fluoro-5-methyl-phenyl | 4.8 | +30.3° (0.53% MeOH) | 135-145 (no salt) | 314.2 |
| 54 | (R) | CH$_2$ | 3,4-dimethyl-phenyl | 3.5 | +31.5° (0.50% MeOH) | 154-156 (no salt) | 310.2 |
| 55 | (R) | CH$_2$ | 2-chloro-4-methyl-phenyl | 3.5 | +29.6° (0.52% MeOH) | 114-116 (no salt) | 330.0 |

-continued

| Ex. | stereo-chem. | X | R | HPLC rt (min) | $[\alpha]_D^{rt}$ | mp. °C. (salt) | M + H$^+$ |
|---|---|---|---|---|---|---|---|
| 56 | (R) | single bond | 2-fluoro-4-methyl-phenyl | 3.4 | nd | 126-130 (no salt) | 300.2 |
| 57 | (R) | CH$_2$ | 2-chloro-5-methyl-phenyl | 3.5 | nd | nd (no salt) | 330.3 |

EXAMPLE 58

Preparation of (R)-3-(6-p-Tolyl-pyridin-3-yloxy)-1-aza-bicyclo[2.2.2]octane

Bromine (18.0 ml, 353.7 mmol) is slowly added to a soln. of 2-amino-5-chloropyridine (15.0 g, 116.7 mmol) in 47% aq. HBr (75.0 ml) at –10° C. An aq. soln. of NaNO$_2$ (28.1 g, 407.3 mmol) is slowly added. The mixture is stirred for 1 h at –10 to –5° C., then for 1 h at 5° C. The mixture is neutralised with 5M aq. NaOH soln. maintaining the temperature below 25° C. The precipitate is filtered and recrystallized from pentane to give 2-bromo-5-chloropyridine. 2-Bromo-5-chloropyridine (5.0 g, 26.0 mmol), p-tolylboronic acid (4.0 g, 29.4 mmol) and tetrakis(triphenylphosphine)palladium (1.44 g, 1.2 mmol) are dissolved in toluene:EtOH 9:1 (1375 ml). A 2M aq. Na$_2$CO$_3$ soln. (62.5 ml) is added to the reaction mixture. The mixture is stirred at 90° C. for 24 h, cooled to rt and filtered over celite. The toluene layer is separated and washed with brine. The aq. layers are extracted with AcOEt. The combined organic extracts are dried over MgSO$_4$ and filtered. The filtrate is evaporated to give a brown solid which is purified by FC (silica gel, eluent toluene) to give 5-chloro-2-tolyl-pyridine. (R)-3-Quinuclidinol (2.97 g, 23.4 mmol) is added to a suspension of NaH (0.96 g of a 60% dispersion in mineral oil, 22.8 mmol) in DMF (90 ml). The mixture is stirred for 1 h at rt. 5-Chloro-2-p-tolyl-pyridine (4.00 g, 19.6 mmol) is added and the mixture is heated for 135 h at 135° C. The reaction mixture is diluted with toluene and washed with 1M aq. NaOH soln. and brine. The aq. layers are re-extracted with toluene (3×). The combined organic extracts are dried over MgSO$_4$ and filtered. The filtrate is evaporated to give a brown oil which is purified by FC (silica gel, eluents: AcOEt, then AcOEt/MeOH/NEt$_3$ 87:10:3) and recrystallized from CH$_3$CN to give (R)-3-(6-p-tolyl-pyridin-3-yloxy)-1-aza-bicyclo[2.2.2]octane; mp ° C.: 110-112; $[\alpha]_D^{rt}$=+21.2° (0.50, MeOH), M+H$^+$295.2.

The following compounds of formula I wherein —O—Y—R is

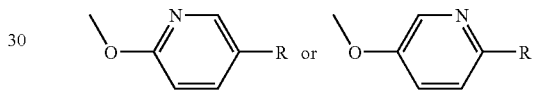

can be prepared in analogy to Example 58:

| Ex. | stereo-chem. | X | —O—Y— | R | HPLC rt (min) | $[\alpha]_D^{rt}$ | mp. ° C. (salt) | M + H$^+$ |
|---|---|---|---|---|---|---|---|---|
| 59 | rac. | CH$_2$ | | phenyl | 6.8 | N/A | 75-80 (no salt) | 281.2 |
| 60 | (R) | CH$_2$ | | phenyl | 5.4 | +34.6° (1.0% MeOH) | 78-81 (no salt) | 281.2 |
| 61 | (R) | CH$_2$ | | phenyl | 4.2 | –19.1 (0.5% MeOH) | 226-236 (HCl salt) | 281.2 |
| 62 | (R) | CH$_2$ | | 3-trifluoro-methyl-phenyl | 3.7 | nd | nd (no salt) | 349.2 |
| 63 | (R) | CH$_2$ | | 2-chloro-phenyl | 3.3 | –18.7 (0.5% MeOH) | nd (HCl salt) | 315.2 |
| 64 | (R) | CH$_2$ | | thiophen-2-yl | 4.3 | nd | 220-237 (phosphate salt) | 287.2 |

-continued

| Ex. | stereo-chem. | X | —O—Y— | R | HPLC rt (min) | $[\alpha]_D^{rt}$ | mp. °C. (salt) | M + H+ |
|---|---|---|---|---|---|---|---|---|
| 65 | (R) | CH₂ | pyridine-O- | o-tolyl | nd | −22.0 (0.5% MeOH) | 200-250 (HCl salt) | 295.2 |
| 66 | (R) | CH₂ | pyridine-O- | m-tolyl | 3.2 | −11.2 (0.5% MeOH) | 204-211 (phosphate salt) | 295.2 |
| 67 | (R) | CH₂ | pyridine-O- | 2,3-dimethyl-phenyl | 3.1 | nd | nd (no salt) | 309.2 |
| 68 | (R) | CH₂ | pyridine-O- | 4-ethyl-phenyl | 3.4 | nd | 178-200 (phosphate salt) | 309.3 |
| 69 | (R) | CH₂ | pyridine-O- | 3,4-dimethyl-phenyl | 3.3 | nd | nd (no salt) | 309.2 |
| 70 | (R) | CH₂ | pyridine-O- | 2-chloro-4-methyl-phenyl | 3.5 | +13.0 (0.52% MeOH) | 94-99 (no salt) | 329.0 |
| 71 | (R) | single bond | pyridine-O- | p-tolyl | 3.0 | nd | 125-127 (no salt) | 261.0 |
| 72 | (R) | CH₂ | pyridine-O- | 1-naphthyl | 3.4 | nd | 146-151 (no salt) | 331.0 |
| 73 | (R) | CH₂ | pyridine-O- | 2-naphthyl | 3.5 | nd | nd (no salt) | 331.0 |
| 74 | (R) | CH₂ | pyridine-O- | 2-chloro-5-methyl-phenyl | 3.4 | nd | nd (no salt) | 329.3 |

HPLC Conditions:

for Examples 1-21, 27-29, 32, 33, 35-38, 41-46, 48-53:: Column Phenomenex Luna or Kingsorb C18, 30×4.6 mm, 3 μM. Gradient (A {H₂O+0.08% HCOOH} B CH₃CN): 0 to 5 min: A:B 100:0 to 80:20, 5 to 10 min: 80:20 to 0:100, flow 3.0 ml/min.

for Examples 22-26 Column Waters Xterra MS C18, 50×2.1 mm, 2.5 μM. Gradient (A:{H₂O+0.02% TFA}, B:{CH₃CN+ 0.02% TFA}): 0 to 2 min: A:B 90:10 to 5:95; 2 to 4 min: 5:95, 4 to 5.5 min 5:95 to 10:90, 5.5 to 6 min: 10:90 to 90:10, 6 to 7 min: 90:10, flow 0.35 ml/min.

for Examples 30, 31, 34, 39, 40, 47, 54-74: Column Waters Xterra MS C18, 150×2.1 mm, 3.5 μM. Gradient (A:{H₂O+ 0.02% TFA}, B:{CH₃CN+0.02% TFA}): 0 to 3 min: A:B 90:10 to 10:90; 3 to 8 min: 10:90, 8 to 9 min: 10:90 to 90:10, 9 to 15 min: 90:10, flow 0.35 ml/min

EXAMPLE 75

Preparation of R-3-(6(2-fluoro-4-methyl-phenyl)-pyridazin-3-yloxy)-1-aza -bicyclo[2.2.2]octane A solution of (R)-(−)-3-quinuclidinol (0.742 g, 5.84 mmol) in dry DMP (5 ml) is added slowly to a suspension of sodium hydride (60% in mineral oil, 0.234 g, 5.84 mmol) in DMF (5 ml) and stirred at 50° C. for 2 h. The reaction mixture is cooled down to rt and a solution of 3-chloro-6-(2-fluoro-4-methyl-phenyl)-pyridazine (1.05 g, 4.49 mmol) in DMF (10 ml) is added. The resulting reaction mixture is stirred for 24 h, quenched by the addition of H₂O and evaporated in high vac to give a orange residue. To the residue is added H₂O (100 ml and extracted with EtOAc (3×50 ml). The organic extracts are combined, washed with H₂O (100 ml), dried over MgSO₄ (anhydrous) and evaporated under reduced pressure to give a yellow solid, which is purified by chromatography, affording the title product, HPLC rt (min): 4.7; mp ° C.: 128-130; $[\alpha]_D^{rt}=+37°$ (0.1%, MeOH).

The following compounds of formula I wherein Y is

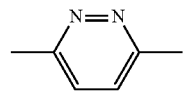

can be prepared in analogy to Example 75:

| Ex. | stereo-chem. | X | R | HPLC rt (min) | $[\alpha]_D^{rt}$ | mp. ° C. | M + H⁺ |
|---|---|---|---|---|---|---|---|
| 76 | (R) | CH₂ | 4,5-dimethyl-2-fluoro-phenyl | 5.5 | +36° (0.1% MeOH) | 108-110 | 328.3 |
| 77 | (R) | CH₂ | 4-ethylphenyl | 5.7 | +25° (0.1% MeOH) | 148-150 | 310.2 |
| 78 | (R) | CH₂ | 2-fluoro-5-trifluoromethyl-phenyl | 6.9 | +37° (0.5% MeOH) | 138-140 | 368.2 |
| 79 | (R) | CH₂ | 3,4-OCH₂O-phenyl | 5.6 | +49° (0.1% MeOH) | 180-182 | 326.2 |
| 80 | (R) | CH₂ | 3-methoxy-phenyl | 5.8 | +36° (0.1% MeOH) | 142-144 | 312.2 |
| 81 | (R) | CH₂ | 2-fluoro-4-methoxy-phenyl | 4.4 | +28° (0.1% MeOH) | 118-120 | 330.3 |
| 82 | (R) | CH₂ | 4-difluoromethoxy-phenyl | 4.8 | +27° (0.1% MeOH) | 153-155 | 348.3 |
| 83 | (R) | CH₂ | 4-methoxy-phenyl | 5.8 | +58° (0.1% MeOH) | 154-156 | 312.2 |
| 84 | (R) | CH₂ | 4-isopropyl-phenyl | 5.7 | +53° (0.1% MeOH) | 164-166 | 324.29 |

Step 75.1: Preparation of 2-fluoro-4-methylbenzene boronic acid

To a mixture of toluene (160 ml) and THF (40 ml) are added triisopropyl borate (13.56 ml, 58.42 mmole) and 3-fluoro-4-bromotoluene (10.0 g, 48.69 mmole). The mixture is cooled down to −40° C. and n-Butyllithium (2.5M in hexane) (23.4 ml, 58.42 mmole) is added slowly over 1 h and the mixture is stirred for an additional hour while the temperature is held at −40° C. The acetone/dry ice bath is removed and the reaction mixture is allowed to warm to −20° C. before a 2.5M HCl solution (20 ml) is added. When the mixture reached rt, the aqueous layer is extracted with EtOAc (3×50 ml), organic extracts are combined, dried over MgSO₄ (anhydrous) and evaporated under reduced pressure to give a yellow solid, which is recrystalilsed from acetonitrile, affording the title product.

Step 75.2: Preparation of 3-Chloro-6-(2-fluoro-4-methyl-phenyl)-pyridazine

To a solution of 3,6-dichloropyridazine (2.0 g, 13.42 mmole) in 1,4-dioxane (20 ml) are added Pd₂(dba)₃ (0.21 g, 0.2 mmole), P(ᵗBu)₃ (0.122 g, 0.6 mmole) in 1,4-dioxane (1 ml), KF (2.57 g, 44.3 mmole) and 2-fluoro-4-methylbenzeneboronic acid (step 31.1, 2.68 g, 17.45 mmole). The resulting mixture is heated at 120° C. for 48 h. The reaction mixture is filtered through celite and washed pad with EtOAc. The filtrate is washed with H₂O, dried over MgSO₄ (anhydrous) and evaporated under reduced pressure to give a brown solid, which is purified by chromatography, affording the title product.

EXAMPLE 85

The following compounds of formula I wherein Y is

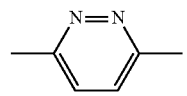

can be prepared in analogy to Example 75:

| Ex. | stereo-chem. | X | R |
|---|---|---|---|
| 85a | (R) | CH₂ | 3,4-dimethyl-phenyl |
| 85b | (R) | CH₂ | 4-methyl-phenyl |
| 85c | (R) | CH₂ | 3-methyl-phenyl |
| 85d | (R) | CH₂ | 2,5-difluoro-4-methyl-phenyl |
| 85e | (R) | CH₂ | 2-fluoro-5-methyl-phenyl |
| 85f | (R) | CH₂ | 3-trifluoromethoxy-phenyl |
| 85g | (3R,4S) | bond | 2-fluoro-4-methyl-phenyl |
| 85h | (3S,4R) | bond | 2-fluoro-4-methyl-phenyl |
| 85i | (R) | CH₂ | 2,5-difluoro-phenyl |
| 85j | (R) | CH₂ | 4-n-propyl-phenyl |
| 85k | (R) | CH₂ | 2-chloro-4-methyl-phenyl |
| 85l | (R) | CH₂ | indan-5-yl |
| 85m | (R) | CH₂ | 2-thienyl |
| 85n | (R) | CH₂ | 6-tetralinyl |
| 85o | (R) | CH₂ | 2-naphthyl |
| 85p | (R) | CH₂ | 2-benzothienyl |
| 85q | (R) | CH₂ | 3-thienyl |
| 85r | (R) | CH₂ | 1-naphthyl |

EXAMPLE 86

Soft Capsules 5000 soft gelatin capsules, each comprising as active ingredient 0.05 g of one of the compounds of formula I mentioned in the preceding Examples, are prepared as follows:

Composition

| Active ingredient | 250 g |
|---|---|
| Lauroglycol | 2 litres |

Preparation process: The pulverized active ingredient is suspended in Lauroglykol® (propylene glycol laurate, Gattefossé S. A., Saint Priest, France) and ground in a wet pulverizer to produce a particle size of about 1 to 3 μm. 0.419 g portions of the mixture are then introduced into soft gelatin capsules using a capsule-filling machine.

The invention claimed is:

1. The compound of formula I

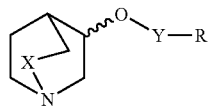
(I)

wherein
X is CH$_2$ or a single bond;
Y is a group of formula

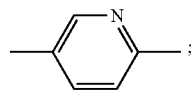

and
R is phenyl, naphthyl, tetrahydronaphthyl, indanyl, thienyl, benzothienyl, furanyl, benzofuranyl and isobenzofuranyl, which in each case can be unsubstituted or mono-, di- or trisubstituted by halogen, cyano, formyl, acetyl, C$_1$-C$_3$alkoxycarbonyl, N,N-di-(C$_1$-C$_3$alkyl) carbamoyl, phenyl, phenoxy, methylendioxy, ethylendioxy; or
C$_1$-C$_4$alkyl, C$_2$-C$_4$alkenyl, C$_2$-C$_4$alkinyl or C$_1$-C$_4$alkoxy, which radicals themselves can be unsubstituted or mono-, di- or trisubstituted by halogen;
in free base or acid addition salt form.

2. The compound of formula I according to claim 1, wherein
X and Y are as defined in claim 1, and
R is
(a) phenyl which is unsubstituted or mono-, di- or trisubstituted by halogen, cyano, methylendioxy,
C$_1$-C$_4$alkyl, which is unsubstituted or mono-, di- or trisubstituted by halogen, or
C$_1$-C$_4$alkoxy, which is unsubstituted or mono-, di- or trisubstituted by halogen,
(b) naphthyl, indanyl, tetralinyl or
(c) furanyl, benzofuranyl, isobenzofuranyl, benzothienyl or thienyl,
in free base or acid addition salt form.

3. The compound of formula I according to claim 1, wherein
X and Y are as defined in claim 1, and
R is
(a) phenyl which is unsubstituted or mono-, di- or trisubstituted by halogen, cyano, methylendioxy,
C$_1$-C$_4$alkyl, which is unsubstituted or mono-, di- or trisubstituted by halogen, or
C$_1$-C$_4$alkoxy, which is unsubstituted or mono-, di- or trisubstituted by halogen,
(b) naphthyl, or
(c) furanyl, benzofuranyl, isobenzofuranyl, or thienyl,
in free base or acid addition salt form.

4. A process for the preparation of the compound of formula I as defined in claim 1, or a salt thereof, which comprises the step of reacting a compound of formula II

(II)

wherein Y and R are as defined in claim 1 and z is a leaving groups, with a compound of formula III

(III)

wherein X is as defined in claim 1,
and recovering the so obtained compound of formula I in free base or acid addition salt form.

5. A pharmaceutical composition comprising the compound according to claim 1 in free base or pharmaceutically acceptable acid addition salt form, in association with a pharmaceutical carrier or diluent.

6. A pharmaceutical composition comprising the compound according to claim 2 in free base or pharmaceutically acceptable acid addition salt form, in association with a pharmaceutical carrier or diluent.

7. A pharmaceutical composition comprising the compound according to claim 3 in free base or pharmaceutically acceptable acid addition salt form, in association with a pharmaceutical carrier or diluent.

8. The compound of formula I according to claim 1, selected from the group consisting of
(R)-3-(6-p-tolyl-pyridin-3-yloxy)-1-aza-bicyclo[2.2.2] octane,
(racemic)-3-(5-phenyl-pyridin-2-yloxy)-1-aza-bicyclo [2.2.2]octane,
(R)-3-(5-phenyl-pyridin-2-yloxy)-1-aza-bicyclo[2.2.2] octane,
(R)-3-(6-phenyl-pyridin-3-yloxy)-1-aza-bicyclo[2.2.2] octane,
(R)-3-(6-(3-trifluoromethyl-phenyl)-pyridin-3-yloxy)-1-aza-bicyclo[2.2.2]octane,
(R)-3-(6-(2-chloro-phenyl)-pyridin-3-yloxy)-1-aza-bicyclo[2.2.2]octane,
(R)-3-(6-thiophen-2-yl)-pyridin-3-yloxy)-1-aza-bicyclo [2.2.2]octane,
(R)-3-(6-o-tolyl-pyridin-3-yloxy)-1-aza-bicyclo[2.2.2] octane,
(R)-3-(6-m-tolyl-pyridin-3-yloxy)-1-aza-bicyclo[2.2.2] octane,
(R)-3-(6-(2,3-dimethyl-phenyl)-pyridin-3-yloxy)-1-aza-bicyclo[2.2.2]octane, (R)-3-(6-(4-ethyl-phenyl)-pyridin-3-yloxy)-1-aza-bicyclo[2.2.2]octane, (R)-3-(6-(3,4-dimethyl-phenyl)-pyridin-3-yloxy)-1-aza-bicyclo[2.2.2]octane, (R)-3-(6-(2-chloro-4-methyl-phenyl)-pyridin-3-yloxy)-1-aza-bicyclo[2.2.2]octane, (R)-3-(6-p-tolyl-pyridin-3-yloxy)-1-aza-bicyclo[2.2.1]heptane, (R)-3-(6-(1-naphthyl)-pyridin-3-yloxy)-1-aza-bicyclo[2.2.2]octane, (R)-3-(6-(2-naphthyl)-pyridin-3-yloxy)-1-aza-bicyclo[2.2.2]octane and (R)-3-(6-(2-chloro-5-methyl-phenyl)-pyridin-3-yloxy)-1-aza-bicyclo[2.2.2]octane; in free base or acid addition salt form.

9. The compound of formula I according to claim 1, selected from the group consisting of (R)-3-(6-p-tolyl-pyridin-3-yloxy)-1-aza-bicyclo[2.2.2]octane, (R)-3-(6-phenyl-pyridin-3-yloxy)-1-aza-bicyclo[2.2.2]octane, (R)-3-(6-(4-ethyl-phenyl)-pyridin-3-yloxy)-1-aza-bicyclo[2.2.2]octane, and (R)-3-(6-(3,4-dimethyl-phenyl)-pyridin-3-yloxy)-1-aza-bicyclo [2.2.2]octane; in free base or acid addition salt form.

10. The compound (R)-3-(6-p-tolyl-pyridin-3-yloxy)-1-aza-bicyclo[2.2.2]octane, in free base or acid addition salt form.

11. The compound (R)-3-(6-phenyl-pyridin-3-yloxy)-1-aza-bicyclo[2.2.2]octane, in free base or acid addition salt form.

12. The compound (R)-3-(6-(4-ethyl-phenyl)-pyridin-3-yloxy)-1-aza-bicyclo[2.2.2]octane, in free base or acid addition salt form.

13. The compound (R)-3-(6-(3,4-dimethyl-phenyl)-pyridin-3-yloxy)-1-aza-bicyclo[2.2.2]octane, in free base or acid addition salt form.

* * * * *